(12) United States Patent
Marcoz et al.

(10) Patent No.: US 12,311,152 B2
(45) Date of Patent: May 27, 2025

(54) INJECTION MONITORING MODULE

(71) Applicant: BIOCORP PRODUCTION S.A.S., Issoire (FR)

(72) Inventors: Alain Marcoz, Issoire (FR); Lionel Aldon, Issoire (FR)

(*) Notice: Subject to any disclaimer, the term of this patent is extended or adjusted under 35 U.S.C. 154(b) by 748 days.

(21) Appl. No.: 17/594,632

(22) PCT Filed: Apr. 26, 2019

(86) PCT No.: PCT/IB2019/000493
§ 371 (c)(1),
(2) Date: Oct. 25, 2021

(87) PCT Pub. No.: WO2020/217076
PCT Pub. Date: Oct. 29, 2020

(65) Prior Publication Data
US 2022/0088312 A1    Mar. 24, 2022

(51) Int. Cl.
*A61M 5/315* (2006.01)
(52) U.S. Cl.
CPC ...... *A61M 5/3155* (2013.01); *A61M 5/31553* (2013.01); *A61M 5/31568* (2013.01);
(Continued)
(58) Field of Classification Search
CPC ...... A61M 2205/35; A61M 2205/0272; A61M 2205/3317; A61M 2205/3561;
(Continued)

(56) References Cited

U.S. PATENT DOCUMENTS

2014/0276583 A1   9/2014  Chen et al.
2015/0246179 A1*  9/2015  Zur .................. G16H 40/67
                                          604/207
(Continued)

FOREIGN PATENT DOCUMENTS

CN   1684729 A    10/2005
CN   202105264 U   1/2012
(Continued)

OTHER PUBLICATIONS

Screen captures from YouTube video clip entitled "Running your Arduino on a Single AA Battery", uploaded on Mar. 15, 2018 by Indrek (@IndrekL) . Retrieved from internet: https://www.youtube.com/watch?v=iDGtwtcSGyU (Year: 2018).*
(Continued)

*Primary Examiner* — Michael J Tsai
*Assistant Examiner* — Isabella S North
(74) *Attorney, Agent, or Firm* — Patshegen IP; Moshe Pinchas

(57) ABSTRACT

An injection monitoring module adapted and configured to be removably attached to a proximal extremity of an injection pen system for delivery of a drug. The monitoring module comprises a hollow main body adapted and configured to be coaxially mounted on, and engage in co-rotation with, a dose setting wheel of the pen injection system, and a central longitudinal bore with a proximal extremity and a distal extremity and an injection monitoring system located in the bore at a proximal extremity thereof. An injection monitoring system is movable within the bore along a central longitudinal, axis thereof from a first monitoring position in which the injection monitoring system is not in abutting contact with a proximal surface of an injection activator of the injection pen system, to a second monitoring position in which the injection monitoring system is in (Continued)

abutting contact with the proximal surface of the injection activator.

17 Claims, 6 Drawing Sheets

(52) U.S. Cl.
CPC ... *A61M 5/3158* (2013.01); *A61M 2205/0272* (2013.01); *A61M 2205/3317* (2013.01); *A61M 2205/50* (2013.01); *A61M 2205/8206* (2013.01)

(58) Field of Classification Search
CPC .......... A61M 2205/50; A61M 2205/52; A61M 2205/8206; A61M 2205/82; A61M 5/20; A61M 5/24; A61M 5/3155; A61M 5/31553; A61M 5/31568; A61M 5/3158; A61M 5/31578; A61M 5/31528; A61M 5/31545; A61M 2205/3327; A61M 5/31573; A61M 2005/3125; A61M 5/31551; A61M 2005/31588; G16H 20/17
USPC .................................. 604/134, 131, 135, 136
See application file for complete search history.

(56) References Cited

U.S. PATENT DOCUMENTS

| | | | |
|---|---|---|---|
| 2016/0015903 A1 | 1/2016 | Madsen et al. | |
| 2018/0154086 A1 | 6/2018 | Toporek | |
| 2020/0188601 A1 * | 6/2020 | Jung | ................. A61M 5/31568 |

FOREIGN PATENT DOCUMENTS

| | | | | |
|---|---|---|---|---|
| CN | 106714878 B | 4/2020 | | |
| CN | 107106785 B | 5/2021 | | |
| CN | 107921217 B | 3/2022 | | |
| EP | 2644217 A1 | 10/2013 | | |
| EP | 3545995 A1 * | 10/2019 | ............. | A61M 5/20 |
| JP | 2016514249 A | 5/2016 | | |
| JP | 2018517502 A | 7/2018 | | |
| WO | 2014128156 A1 | 8/2014 | | |
| WO | 2017013464 A1 | 1/2017 | | |
| WO | WO-2017013463 A1 * | 1/2017 | ........ | A61M 5/31533 |
| WO | 2018013419 A1 | 1/2018 | | |
| WO | 2019001919 A1 | 1/2019 | | |
| WO | WO-2019057911 A1 * | 3/2019 | .......... | A61M 5/2033 |

OTHER PUBLICATIONS

ISR; European Patent Office; NL; Dec. 13, 2019.

* cited by examiner

INJECTION MONITORING MODULE

The present invention relates generally to monitoring systems for injectable drug delivery devices, and in particular to injection monitoring for injection pen systems.

Injection monitoring is a well known field associated with injectable drug delivery devices, especially with regard to infusion systems, for example. Over time, such monitoring systems have been transferred more recently to injection pen systems for delivery of a drug, enabling users of such pen injection systems, and health care professionals involved in the treatment and follow-up of such patients, to monitor more closely their own injection regimes, and in many cases, the doses actually administered, in an attempt to lead to better healthcare outcomes. These developments have been accompanied by the increased associated use of software and portable communications devices such as tablets or smartphones, which have been programmed to receive information from, and interact with, the monitoring systems in order to provide information to the user or healthcare professional on-the-fly, or at regular intervals via appropriate communications units included in the monitoring systems.

In regard to pen injection systems in particular, for example, one of the challenges has been to provide easy to use, reliable and fairly failsafe systems that can be adapted to the various different variants of such commercially available pen injection systems, of which there are many. Previous attempts at providing such monitoring systems have usually involved adapting the body of the pen injection system by including electronic components therein along with one or more sensors. One of the major disadvantages of such systems however, is that they tend to make the end product, once all of the electronic components have been integrated, into fairly bulky and unwieldy objects, and thus more difficult to use from a user perspective. Additionally, such modified systems tend to be very specific to a given brand or a manufacturer, and thus of little or no use with other manufacturers. Furthermore, in order to overcome the issues with bulkiness and unwieldiness of the modified pen injection systems, there has been a tendency to attempt to reduce the overall volume of the injection pen bodies as much of possible through miniaturisation of the complex electronic components, which in turn has brought about its own problems, in particular with regard to electromagnetic interference between the various components due to the close proximities of the circuits providing the required or desired integrated functionality. Moving the sensors in such monitoring systems further away from the source of electromagnetic interference only further complicates matters, potentially leading to erroneous readings, or requiring further systems to compensate for the physical separation of the sensors from the other electronic components, such as a micro-controller designed to control and command the various components and manage their interactions.

The injection pen systems in question are well known per se and are commonly equipped with a proximally located dose setting wheel and injection activator, the dose setting wheel being rotatable about a central longitudinal axis of the pen injection system. The wheel is rotated by the user to select the dose of drug to be administered. The pen is generally configured, either mechanically or electro-mechanically to effect an injection upon activation of an injection activator. Such injection activators are quite commonly a simple press or push-button, in mechanical or electrical contact with the dispensing mechanism located within the pen injection system, the pressing of which causes the injection mechanism to fire and inject the drug contained within the pen injection system. In some pen injector systems, the dose setting wheel is configured to rotate not only during dose setting, but also during injection. This is generally achieved through the inclusion of one or more metallic components, such as a helically wound drive spring located within a housing body of the injection pen system and physically coupled to the dose setting wheel. As such metallic elements are relatively large objects in comparison to the electronic component systems that are included in many pen injection systems today, these large metallic objects can further perturb signals that the sensors in such electronic component systems are designed to capture or pick up, rendering the systems potentially less accurate, and/or requiring that complex correction mechanisms be put in place to avoid calculation errors.

Some attempts at overcoming the difficulties of electronic component integration have already been described in the patent literature.

For example, published PCT patent application WO2014128156A1 relates to a sensor assembly having a first rotary sensor part with a plurality of individual electrically conducting sensor areas arranged in a pattern, a second rotary sensor part arranged rotationally relative to the first part, and comprising a plurality of contact structures adapted to be in contact with conducting sensor areas on the first sensor rotary part. The contact structures are configured to engage and connect different sensor areas as the first and second part of the rotary sensor rotate relative to each, the created connections being indicative of a rotational position between the first and second portions. One of the contact structures is an actuatable contact structure being axially moveable relative to the first portion and having a connected position in which the actuatable contact structure is in contact with a sensor area and a disconnected position in which the actuatable contact structure is not in contact with a sensor area. This system is housed within the pen injector body, at least partly within the volume inside the dose setting wheel. The system also comprises a visual display, such as a LCD display located on, or instead of, the injection activator button.

In comparison, published PCT application WO2018013419A1 relates to a dose detection system including a dosing component attached to an actuator and rotationally and axially moveable relative to a coupling component attached to a dose setting member, and comprising a module including an electronic sensor operative to detect a relative rotation of the coupling component and the dosing component to detect a dose delivered by the medication delivery device. The dose detection module is removably coupled to a proximal end of a pen injection system, and is intended to function as a means to detect the amount of medication dispensed by the pen injection system while attached thereto, store the detected dose in memory, and transmit a signal representative of the detected dose to a remote communication device. The system comprises a pair of rotatable and translatable cylinders that interact with each other via electrical contacts provided on the cylinder surfaces to denote various states or positions of the injection administration process including dose setting, the electrical contacts being connected to a collection of electronic components housed on a flexible printed circuit board, disposed in an accordion-style arrangement of superimposed folds within the removably couple body, and which is insulated between the overlapping layers of circuit board by an electrically non-conducting spacer layer to prevent potential electric, electronic and electromagnetic interference.

One immediate observation of the above-described configuration is that despite the use of a folded flexible printed circuit board to provide multiple surfaces on which to position the electronic components, their relative spatial density and positioning with regard to each other has necessitated that non-conducting spacers be provided between the layers of electronic componentry. The immediate consequence of this is an increased height in the module and a necessarily increased complexity of the clip-on dose detection module described therein.

Accordingly, one object of the present invention is to provide an injection monitoring module adapted and configured to be removably attached to a proximal extremity of an injection pen system for delivery of a drug, the injection pen system having a dose setting wheel that can be rotated for setting a dose of drug to be injected, wherein said dose setting wheel also rotates during injection, and wherein the injection monitoring module has a much simpler configuration, whilst at the same time obviating the need for complicated shielding or protecting solutions to counter any unwanted electrical, electronic, or electromagnetic effects caused by the relatively high density of the electronic components within the monitoring module.

Another object of the present invention is to provide an injection monitoring module as above, wherein said module is adapted and configured to detect an injection end point in a pen system having a rotating dose setting wheel that rotates during injection. For the purposes of the present invention, the expression "injection end point" as used herein signifies not only the completion of an injection of a dose of injectable substance such as a drug, where a user injects a required dose of injectable substance in a single operation, but also includes any amount of drug actually ejected by the pen injection system when the injection monitoring module is mounted thereon. This means that if a user carries out a sequence of small repeat injection operations, for example, by repeated, successive activation of the injection activator, a corresponding end point for each injection step will be registered, and a corresponding amount of injectable substance calculated as having been injected or ejected from the pen injection system.

These and other objects of the invention will become readily apparent from the complete reading of the current specification.

According to any of the above objects therefore, there is provided an injection monitoring module adapted and configured to be removably attached to a proximal extremity of an injection pen system for delivery of a drug, the injection pen system being equipped with a proximally located dose setting wheel and an injection activator, the dose setting wheel being rotatable about a central longitudinal axis of the pen injection system for dose setting and during injection, the injection monitoring module comprising:

a hollow main body adapted and configured to be coaxially mounted on, and engage in co-rotation with, the dose setting wheel at the proximal extremity of the pen injection system;

the hollow main body comprising a central longitudinal bore with a proximal extremity and a distal extremity; and an injection monitoring system located within the central longitudinal bore of the main body at the proximal extremity thereof and extending beyond said proximal extremity along said longitudinal axis in a proximal direction;

wherein the injection monitoring system is movable within the central longitudinal bore of the main body along the central longitudinal axis from a first monitoring position in which the injection monitoring system is not in abutting contact with a proximal surface of the injection activator, to a second monitoring position in which the injection monitoring system is in abutting contact with a proximal surface of the injection activator.

As used herein, the terms "pen injection system" and "injection pen system" are used interchangeably to designate a generally handheld pen-shaped injection system, such systems being readily well known per se and commercially available for use in the treatment of many various medical indications. These systems are also often generally designed for self-injection of a drug by the user in need of treatment for the given medical indication. This is for example the case with insulin, intended to treat the consequences of diabetes, one such example being the pen injector commercialized under the brand name Lantus® SoloSTAR® by Sanofi-Aventis. However, other drugs also fall into this category, required for example, to address potentially life-threatening situations, and enabling immediate emergency injection of a required drug, such as anaphylactic shock treatments, anticoagulants, opioid receptor agonists and antagonists, and the like, to the extent that it has become a common occurrence for patients suffering from, or susceptible to, such ailments to carry these devices around with them.

The injection pen system, to which the injection monitoring module according to the invention is adapted and configured for removable attachment, is equipped with a proximally located dose setting wheel and an injection activator. The dose setting wheel rotates about a central longitudinal axis of the pen injection system to allow a user to set the dose of medicament for injection. The dose setting wheel is generally rotatable in both a clockwise, and a counter-clockwise direction, these directions corresponding generally to an increase in the selected dose, and a decrease in the selected dose, to be administered, respectively. The injection activator is often represented by a push-button. When a user of the injection system presses the injection activator in a distal direction, a piston is driven which is connected to a plunger in order to expel drug from a chamber within the injection pen body out through a needle that the user has inserted into an appropriate injection site, for example, the skin, fatty tissue, or muscle, depending on the type of drug to be administered. The dose setting wheel is coupled to the injection drive mechanism so that it also rotates as injection of the drug proceeds. The functioning of such injection systems is well known per se in the art.

The injection monitoring module according to the invention, therefore, is adapted and configured to be removably attached to a proximal extremity of such an injection pen system. The expressions "removably attached" or "removably attachable" as might be used in the present specification are to be understood as referring to the possibility of attaching and subsequently removing the injection monitoring module, for example, in the case of transferring the injection monitoring module to another pen injection system, or for example, if the monitoring module is damaged during use and requires replacement. Such attachment and subsequent removability can be achieved by providing coupling means on the monitoring module which engage in a releasable manner with the proximal extremity of the pen injection system, for example via frictional or elastic engagement, or via other releasable fastening means, such as clips, straps, screw threads and corresponding tightening rings, and the like, which engage with either the dose setting wheel, or the injection activator, or both.

Accordingly, in light of the above, the removably attachable injection monitoring module comprises a hollow main body adapted and configured to be coaxially mounted on, and engage in co-rotation with, the dose setting wheel at the proximal extremity of the pen injection system.

The hollow main body of the injection monitoring module comprises a central longitudinal bore with a proximal extremity and a distal extremity. The distal extremity of the bore is preferably configured and dimensioned to elastically engage with, for example, via friction, and surround, an outer surface of the dose setting wheel of the pen injection system, such that if the hollow main body is rotated, then so does the dose setting wheel in the same direction, and to substantially the same or identical degree of rotation, and conversely, if the dose setting wheel is rotated, then so does the hollow main body. In this way, the hollow main body can be said to co-rotate with the dose setting wheel. The hollow main body is appropriately made of any suitable material, for example of a durable polymer or plastic material. Advantageously, the hollow body is made of transparent, translucent, or opaque material, in order to enable a user to apprehend and recognise any visual cues, such as light emitting diodes, that might also be provided or integrated into the injection monitoring module, where such cues can be optionally used to indicate various states of operation of the injection monitoring system.

The injection monitoring module also comprises an injection monitoring system located within the central longitudinal bore of the main body at the proximal extremity thereof and extending beyond said proximal extremity along said longitudinal axis in a proximal direction. The injection monitoring system will be described in further detail below, but basically, the injection monitoring system comprises a number of different components and means that provide for monitoring of an injection state, for example, such as:

initiation of an injection operation;
termination of an injection operation, whereby termination of an injection operation is to be understood to cover both a complete administration of a selected dose of substance to be injected, or discrete injection operations in which a user only injects a part of a dose, or causes a part of the selected dose to be ejected from the pen injection system.

Furthermore, in accordance with an object of the invention, the injection monitoring system is movable within the central longitudinal bore of the main body along the central longitudinal axis from a first monitoring position in which the injection monitoring system is not in abutting contact with a proximal surface of the injection activator, to a second monitoring position in which the injection monitoring system is in abutting contact with a proximal surface of the injection activator.

From the above, it will be understood that the injection monitoring system can be moved from an initial position where there is no physical contact between the monitoring system and the activator button, to a different position where physical contact is established between the monitoring system and the proximal surface of the injection activator. Such movement will generally be a translational movement of the monitoring system along the central longitudinal axis within the bore of the hollow main body from the first position to the second position.

According to another object of the invention, the injection monitoring module comprises a magnetic field producing means. Various means for producing a magnetic field are known, for example, classical magnets, electromagnets, and mixed material magnets. Such magnets are typically made from magnetizable materials, having magnetic or paramagnetic properties, whether naturally or when an electric or other energizing flow traverses or affects said material to produce or induce a magnetic field in said material. Suitable materials can be appropriately selected from:

ferrite magnets, especially sintered ferrite magnets, for example, comprising a crystalline compound of iron, oxygen and strontium;
composite materials consisting of a thermoplastic matrix and isotropic neodymium-iron-boron powder;
composite materials made up of a thermoplastic matrix and strontium-based hard ferrite powder, whereby the resulting magnets can contain isotropic, i.e. non-oriented, or anisotropic, i.e. oriented ferrite particles;
composite materials made of a thermo-hardening plastic matrix and isotropic neodymium-iron-boron powder;
magnetic elastomers produced with, for example, heavily charged strontium ferrite powders mixed with synthetic rubber or PVC, and subsequently either extruded into the desired shape or calendered into fine sheets;
flexible calendered composites, generally having the appearance of a brown sheet, and more or less flexible depending on its thickness and its composition. These composites are never elastic like rubber, and tend to have a Shore Hardness in the range of 60 to 65 Shore D ANSI. Such composites are generally formed from a synthetic elastomer charged with strontium ferrite grains. The resulting magnets can be anisotropic or isotropic, the sheet varieties generally having a magnetic particle alignment due to calendaring;
laminated composites, generally comprising a flexible composite as above, co-laminated with a soft iron-pole plate;
neodymium-iron-boron magnets;
steels made of aluminium-nickel-cobalt alloy and magnetized;
alloys of samarium and cobalt.

Of the above list of magnetic field producing means suitable for use in the present invention, those selected from the group consisting of neodymium-iron-boron permanent magnets, magnetic elastomers, composite materials made up of a thermoplastic matrix and strontium-based hard ferrite powder, and composite materials made of a thermo-hardening plastic matrix and isotropic neodymium-iron-boron powder, are preferred. Such magnets are known for their ability to be dimensioned at relatively small sizes whilst maintaining relatively high magnetic field strength.

Whilst the magnetic field producing means can be of any suitable general shape, for example disk-shaped, including circular, ellipsoid, or any other suitable polygonal shape, it preferably has only a single dipole, with a single pair of diametrically opposing north and south magnetic poles. Although the magnetic field producing means can be substantially disk-shaped, such a disk-shape can also include magnets which have an orifice substantially in the centre of the disk to form a ring or annular shaped magnet.

According to one advantageous object of the invention, the magnetic field producing means comprises two diametrically aligned single dipole magnets, in which the magnets are aligned across a diameter of the hollow bore at opposite positions of said diameter and substantially along a circumference of said bore. The term "alignment" or "aligned" as used herein, refers to the poles of the magnets being aligned along a longitudinal axis of each magnet. Such a configuration can be achieved, for example, through the use of rod-shaped or cylindrical magnets having a first and second ends, a first pole being located substantially at a first end and a second and opposite pole being located substantially at the second end of the rod shaped magnet. Each magnet is then located at opposite positions on a circumference of the hollow bore such that the rods are in longitudinal alignment one with the other. The magnetic poles of each magnet can be respectively be positioned inverted one with respect to the other, for example in a N-S/S-N arrangement or a S-N/N-S arrangement, but preferably and advantageously, the magnetic poles are positioned in a repeat configuration in which the poles are aligned in a N-S/N-S or a S-N/S-N arrangement.

In yet a further object of the invention, the magnetic field producing means is seated immovably within the bore of the hollow main body and around the central longitudinal axis. The term "immovable" here is to be understood as meaning that the magnetic field producing means is located in a fixed position along the central longitudinal axis with regard to the bore of the hollow main body, which also signifies that it does not undergo any longitudinal translational movement within the injection monitoring module. For example, the magnetic field producing means can be located, or integrated into, the material forming the main hollow body with the effect of producing a magnetic field that extends at least partly into the bore of said hollow body.

Alternatively, and advantageously, according to yet another object of the invention, the magnetic field producing means are integrated, inserted, or otherwise introduced, into a separate magnetic field producing means holder body. The holder body in this case is advantageously configured and dimensioned to form a disk, or an annular-shaped disk, i.e. a disk with a hole substantially in its middle. The annular-shaped disk is introduced into the bore of the main hollow body and located therein in a fixed longitudinal position in coaxial alignment with the central longitudinal axis. The disk in such a configuration, when formed as an annular-shaped disk, advantageously projects radially inwardly into the bore from an inner circumferential surface of the bore, creating a reduced bore diameter at the radially innermost end of such a projection.

As the magnetic field producing means is located immovably in the bore of the main hollow body, for example, in the manners and configurations described above, i.e. immovably from a longitudinal translational movement perspective, it will be understood that the magnetic field producing means remains nonetheless free to co-rotate with said main hollow body, albeit about a fixed longitudinal position with regard to the hollow body and central longitudinal axis. This means that when either the dose setting wheel, or the main hollow body, are rotated, the magnetic field producing means is also rotated about the central longitudinal axis to the same extent.

According to another object of the invention, the injection monitoring system is mounted within a selectively engageable, and respectively disengageable, clutch assembly. The expression "clutch assembly" as used in the present specification, refers to an assembly configured to selectively move the injection monitoring system from a first, engaged, position, to a second, disengaged, position, which when taken in context of the present invention, corresponds to the first monitoring position in which the injection monitoring system is not in abutting contact with a proximal surface of the injection activator, and respectively, the second monitoring position in which the injection monitoring system is in abutting contact with the proximal surface of the injection activator. The notions of "engagement", "engageable", "disengagement" and "disengageable", as used in the present specification, are provided to facilitate understanding of how the clutch assembly functions with regard to the injection monitoring system mounted therein, further details of which will be given below. One of the purposes of the clutch assembly is to provide a vehicle or a means by which longitudinal translational movement of the injection monitoring system, along the central longitudinal axis, may be achieved.

According to still another object of the invention, the clutch assembly comprises a first, distal body and a second, proximal body, and further comprises a biasing member located between the first, distal body and the second, proximal body. The first and second bodies are physically connected or bonded to each other, for example via ultrasonic welding, of appropriate locations of the first, distal body and the second, proximal body. The first and second bodies are advantageously dimensioned and configured to fit within the hollow bore of the main body, and be movable therein in translational movement along the central longitudinal axis.

According to yet another object of the invention, the first, distal body, and the second, proximal body of the clutch assembly are connected together along the central longitudinal axis via an elongated hollow connecting member. In this configuration, the elongated hollow connecting member forms a tube between the first, distal body and the second, proximal body. The connecting member can be integrally formed with either the first, distal body, or with the second, proximal body, or alternatively partly with both the first, distal body, and the second, proximal body, and bonded together, or can be formed as a separate, hollow, elongated connecting member which is bonded to both the first, distal body at a proximal end thereof, and the second, proximal body at a distal extremity thereof. Such bonding can be achieved, for example, by ultrasonic welding of the respective distal and proximal bodies, or by assembling and welding the respective distal and proximal bodies with the connecting member when the latter is not formed integrally with any of the first or second bodies.

According to a still further object of the invention, the first, distal body of the clutch assembly is located distally of the magnetic field producing means.

According to yet another object of the invention, the second, proximal body is located proximally of the magnetic field producing means.

From the foregoing, it will be understood that the first, distal body, and the second, proximal body, are optimally located either side of of the magnetic field producing means, and are also connected to each via the elongated hollow connection member, leading to a fixed distance relationship between said first, distal body and said second, proximal body. As has been mentioned above, the magnetic field producing means is located in a fixed relationship within the main hollow body of the injection monitoring module, with the first and second bodies positioned either side thereof, which means that the first and second bodies can only translate longitudinally, either distally, or proximally, from the first position to the second position along said central longitudinal axis along a predetermined distance of travel before one or the other comes into contact with the radially inwardly projecting surface of the annular-shaped disk of the magnetic field producing means.

The biasing member, which is located between the first, distal body and the second, proximal body, and is preferably and advantageously also located proximally of the magnetic field producing means and distally of the second, proximal body. The biasing member is generally a pre-constrained biasing member, such as a spring, and for which an appropriate choice can be made by the skilled person to suit the desired application. For the purposes of the present invention, however, it has been found advantageous that such a pre-constrained biasing member be a flat wire compression spring or a wave spring. Such flat wire compression springs, or wave springs are known generally in the art, and are available, for example, from the Smalley Steel Ring Company, under the CM and CMS range identifications, where CM refers to plain-ended wave springs, and CMS refers to shim-ended wave springs. Such springs are generally either made of carbon steel, or stainless steel.

The biasing member is designed to bias the second, proximal body into the engaged position, i.e. the position when the injection monitoring module is at rest after mounting on the pen injection system, and/or during dose setting, when the dose setting wheel is being rotated to set the dose of drug to administer, and the biasing member adopts a relatively unconstrained configuration. This position is considered to be the engaged position because the biasing member pushes against a distal surface of the proximal body, and a correspondingly proximal surface of the first, distal body is in contacting surface abutment with a distal surface of the magnetic field producing means.

When the biasing member is constrained in the distal direction, for example, when a distal surface of the second, proximal body is moved, or translated, in a longitudinal and distal direction, it bears down on the biasing member, moving it into a constrained configuration, and, due to the solid connection member between the second, proximal body and the first, distal body, causes said first, distal body to move by the same extent, due to the fixed relationship between the two, into a disengaged position, in which a proximal surface of the first, distal body is disengaged from, and no longer in contact with a distal surface of the magnetic field producing means.

According to still yet another object of the invention, the injection monitoring system comprises a single magnetic field sensor.

According to another object of the invention, the single magnetic field sensor is located on the central longitudinal axis, and is movable along said axis from a first proximal position to a second distal position along said axis.

According to yet another object of the invention, the single magnetic field sensor is located on, or within, the first, distal body. As will be readily apparent from the description above with regard to said first, distal body, second, proximal body, biasing means and magnetic field production means, this signifies that the magnetic field sensor is movable from a first proximal position adjacent the magnetic field production means, to a second, distal position, located away from said first position, longitudinally along the central longitudinal axis.

The magnetic field sensor is used to measure the magnetic field produced by the magnetic field producing means. Movement of the sensor along the central longitudinal axis relative to the fixed magnetic field production means is used to calculate the translational position of a reference point along said central longitudinal axis, which reference point can be used to correlate to a zero point, an initialization point, a start point for injection, an end point for injection, and/or a point corresponding to any administered amount of injectable substance, such as a drug, for the injection monitoring system according to the invention.

Means for measuring magnetic fields to determine are known generally in the art. For example, magneto-resistors are a well known means. Such magneto-resistors are often designated by their abbreviations, e.g. AMR, GMR, TMR sensors, which designate the physical mechanisms by which these sensor components function. Giant magnetoresistance (GMR) is a quantum mechanical magnetoresistance effect observed in thin-film structures composed of alternating ferromagnetic and non-magnetic conductive layers. Anisotropic magnetoresistance, or AMR, is said to exist in materials in which a dependence of electrical resistance on the angle between the direction of electric current and direction of magnetization is observed. Tunnel magnetoresistance (TMR) is a magnetoresistive effect that occurs in a magnetic tunnel junction (MTJ), which is a component consisting of two ferromagnets separated by a thin insulator. Resistors that use these various properties are known per se.

In light of the above, the injection monitoring module and/or system according to the invention preferably uses a magnetometer as the magnetic field sensor. Such a magnetometer differs from the GMR, AMR or TMR sensors in that it directly measures magnetic field strength. Magnetometers measure magnetic fields in two main ways: vector magnetometers measure the vector components of a magnetic field, and total field magnetometers or scalar magnetometers measure the magnitude of the vector magnetic field. Another type of magnetometer is the absolute magnetometer, which measures the absolute magnitude or vector magnetic field, using an internal calibration or known physical constants of the magnetic sensor. Relative magnetometers measure magnitude or vector magnetic field relative to a fixed but uncalibrated baseline, and are also called variometers, used to measure variations in magnetic field.

A preferred magnetometer therefore for use in the injection monitoring module according to the present invention is an ultra low-power high performance three axis Hall-effect magnetometer. Whilst it is possible for the magnetometer to be configured to measure magnetic field over three mutually perpendicular or orthogonal axes, it is preferred in the present case that the magnetic field sensor be configured to measure magnetic fields over just two of the three orthogonal axes, for example the X and Z axes, whereby the Y axis is co-axial with the central longitudinal axis and thereby corresponds to the normal along which distance measurements relating to translational movement of the magnetic field sensor along said longitudinal axis can be calculated as indicated above in respect to a reference point position on said axis.

According to yet another object of the invention, the injection monitoring system comprises an electronic component board.

Advantageously, and according to a further object of the invention, the single magnetic field sensor is electrically connected to the electronic component board.

Even more advantageously, the electronic component board comprises an integrated control and data processing unit, such as at least one micro-controller, connected electrically to the magnetic field sensor for processing information received from the magnetic field sensor. The electronic component board can therefore suitably be, for example, a printed circuit board of correspondingly appropriate dimensions. In the configurations envisaged in the present invention, such a printed circuit board is advantageously disk-shaped.

The electronic component board is advantageously, located on, integrated into, or housed within, the first, distal body of the clutch assembly. The integrated control and data processing unit, comprising at least one micro-controller, handles all electrical communication and signalling between the different electronic components of the electronic component board and the magnetic field sensor. It is also responsible for execution of the calculations enabling the precise positional location of the magnetic field sensor to be calculated and determined, as well as handling signals from an autonomous power supply and communication means integrated into the injection monitoring system, and which communicate with a local or remote data processing system, e.g. on a smartphone. It can be programmed remotely, upon first use, or receive information and updates, in a similar way to other electronic devices today containing integrated control and data processing units. Such integrated control and data processing units are known per se, and often integrate a central processing unit, a real time clock, one or more memory storage systems, and optionally communications systems or subsystems, along with other desired components.

According to yet another object of the invention, the magnetic field sensor is located on a proximal face of the electronic component board. In this manner and configuration, the magnetic field sensor, when the injection monitoring module is first mounted on the pen injection system, is almost in abutting contact with the magnetic field producing means. Additionally, and advantageously, the magnetic field sensor is located on the proximal face of the electronic component board as near to the central longitudinal axis as is physically possible, and preferably is located on said central longitudinal axis. The objective with such positioning is to try and avoid, to the extent possible, any need for correction calculations to be carried out by the integrated control and data processing unit, due to a radial positioning displacement of the magnetic field sensor from the central longitudinal axis, thereby increasing accuracy of the corresponding calculations and the precision when determining translational reference points along said axis.

As will be surmised from the preceding description, another object of the invention is an injection monitoring module wherein, in the monitoring system, the first, distal body is an electronic component board holder body. and the electronic component board is consequently located within the component board holder body.

As has been mentioned briefly above, the electronic component board is powered by an autonomous power supply. According to one object of the invention therefore, the injection monitoring system comprises a removable and/or rechargeable power supply. Such a removable, autonomous, power supply can usefully be for example a lithium ion battery, which can be easily exchanged when depleted, or alternatively, a rechargeable battery, which can be charged up when depleted for example via a corresponding charging port provided in the injection monitoring module and connected to the rechargeable battery, both types of battery being generally known to the skilled person.

Advantageously therefore, and according to still yet another object of the invention, the second, proximal body is a power supply holder body, with the power supply being preferably located within the power supply holder body. The second, proximal body, as exemplified here as the power supply holder body, is helpfully and advantageously closed at a proximal end thereof by a removable cap, configured and dimensioned to be pushed by the thumb or finger of a user when activating the injection monitoring system. The cap usefully covers the power supply, preventing ingress of dust and/or water or humidity, and is crafted to be push-fit or elastically engageable with the second, proximal body, but is also by the same token removable in order to allow access to the power supply, for example, in order to change the battery.

From the above and preceding paragraphs, it will be apparent that power supply is in the second, proximal body, and the electronic component board is in the first, distal body. The two are advantageously connected electrically via the elongated hollow connecting member, wherein the electrical connection, for example, standard copper wiring, is located within the hollow, elongated connection member. The electrical connection between the power supply and the electronic component board is configured and dimensioned within the elongated connection member to avoid any detachment or interruption of the electrical connection, even when the injection monitoring system is rotating in co-axial rotation with the dose setting wheel. Using the elongated connection member as a conduit for said electrical connection is therefore extremely advantageous, as said elongated connection member lies along the central longitudinal axis, meaning that even if a user twists and turns the dose setting wheel, and correspondingly mounted injection monitoring system, in a variety of alternating or successive rotations, the electrical connection will be protected from any substantial rotation, reducing the risk of breakage or disconnection.

According to another object of the invention, and as will be apparent from the preceding description of the relative movements and positions of the various components, the injection monitoring system comprises an arrangement in which the magnetic field producing means comprises a distal surface that is in contact with a proximal surface of the electronic component board body when the clutch assembly is in the first, engaged position, and wherein said proximal surface of the electronic component board body is axially spaced apart, along the central longitudinal axis, from said distal surface of the magnetic field producing means when the clutch assembly is in the second, disengaged position.

Additionally, and advantageously, the first monitoring position is a position in which the proximal surface of the electronic component board body is in abutting contact with the distal surface of the magnetic field production means, and the second monitoring position is a position in which the distal surface of the injection monitoring system is in abutting contact with the proximal surface of the injection activator of the pen injection system. In such a configuration, when the biasing member is constrained in a distal direction along the longitudinal axis, the proximal surface of the electronic component board body is moved distally away from abutting contact with the distal surface of the magnetic field means, i.e. away from the first position, until the point where the distal surface of the electronic component board body comes into contact with, and/or abuts, the proximal surface of the injection activator of the pen injection system. The magnetic sensor relays the changes in measured magnetic field to the integrated control and data processing unit as the sensor is moved along the central longitudinal axis away from from the magnetic field producing means until abutment with the injection activator, this distance being a few millimetres, for example, around 15 millimetres. Consequently, the whole injection monitoring module can be manufactured to comprise a total length, from a distal end of the hollow main body to the proximal end of the push cap cover, of a few tens of millimetres, for example, approximately 20 to 30 millimetres in total length.

According to yet another object of the invention, there is provided a process for calculating an actual amount of drug ejected or injected from a pen injection system comprising:
  mounting an injection monitoring module comprising an injection monitoring system as substantially described in the present specification to a proximal extremity of an injection pen system for delivery of a drug, the injection pen system being equipped with a proximally located dose setting wheel and an injection activator, the dose setting wheel being rotatable about a central longitudinal axis of the pen injection system for dose setting and during injection;

setting a dose via rotation of the dose setting wheel;

activating the injection activator to effect an injection;

determining an injected dose from a translational movement of the injection monitoring system caused by activation of the injection activator, from a first monitoring position in which the injection monitoring system is not in abutting contact with a proximal surface of the injection activator, to a second monitoring position in which the injection monitoring system is in abutting contact with a proximal surface of the injection activator.

BRIEF DESCRIPTION OF THE FIGURES

The invention will now be described in more detail with regard to the accompanying figures, provided for the purpose of illustration and exemplification, in which.

DETAILED DESCRIPTION

Figure 1:
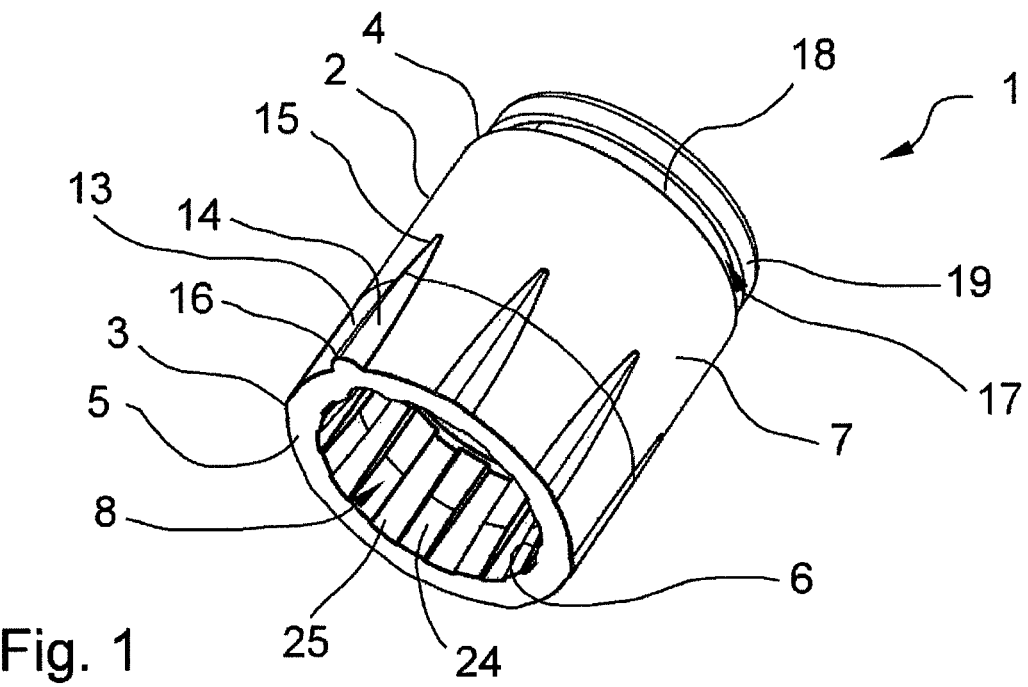
FIG. 1 is a schematic, perspective representation of an injection monitoring module according to the invention for a handheld pen-type injection system.

Turning now to FIG. 1, a schematic perspective representation of an injection monitoring module (1) according to the invention is illustrated. The injection monitoring module comprises a hollow main body (2), having a distal extremity (3) and a proximal extremity (4). The hollow main body (2) has a circumferential wall (5) with an inner (6) and outer surface (7), thereby defining a central bore (8) of the main hollow body (2) extending from the distal extremity (3) to the proximal extremity (4). The distal extremity (3) is open, allowing the injection monitoring module (1) to be inserted over, and surround, a proximal extremity (9) of a pen injection system (10) having a dose setting wheel (11) and an injection activator button (12). The hollow main body (2) is provided with an indexation shoulder (13) on the outer surface (7) of the hollow main body (2) to facilitate alignment of the body (2) with a corresponding zero-point position on the dose setting wheel (11) of the pen injection system (10), and corresponding to a dose setting of zero. The indexation shoulder (13) comprises a raised region of material constituting the main body (2) and extending in a slope (14) of increasing thickness of said body material from a proximal end (15) to a distal end (16). At the proximal extremity (4) of the main body (2), the bore (8) is substantially closed by a clutch assembly (17), of which only a proximal body (18) and covering cap (19), forming part of an injection monitoring system (20), are visible.

Figure 2:
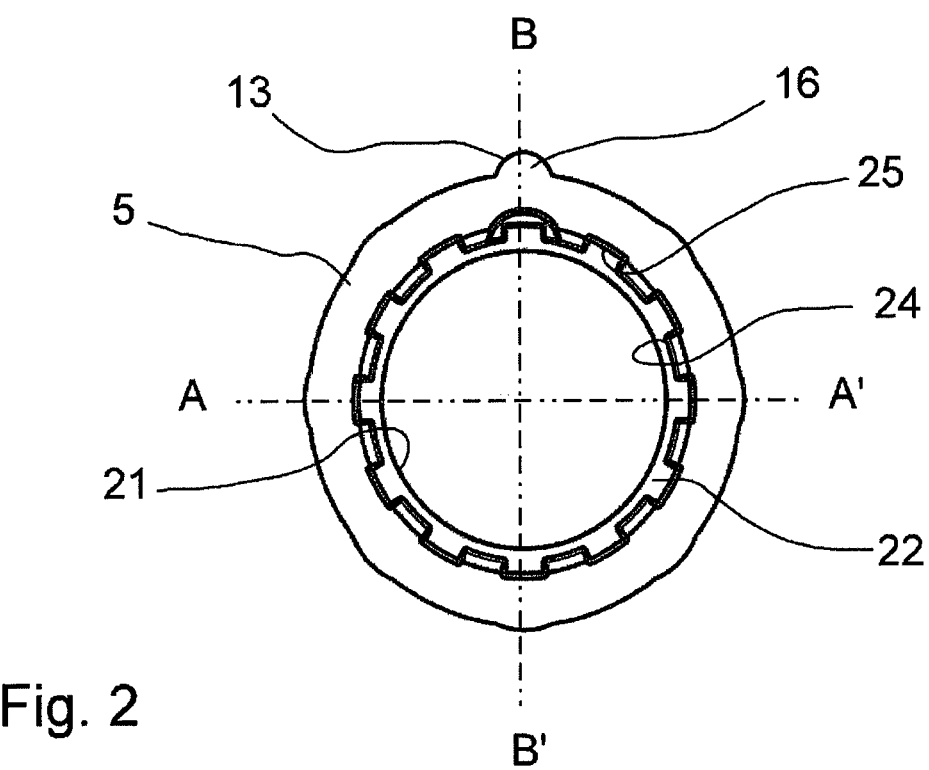
FIG. 2 is a schematic, end on representation of the injection monitoring module of FIG. 1, seen from a distal end thereof.

FIG. 2 is an end on view of the injection monitoring module, as seen from the distal extremity (3) of the main body (2). The indexation shoulder (13) of raised body material can be seen, projecting upwardly from the outer surface (7) of the circumferential wall (5) of the main body (2). An annular flange (21), projecting radially inwardly from the inner surface (6) of the body (2), and thereby narrowing the diameter of the bore (8), provides a means for limiting any proximal movement of the injection monitoring module (1) when the body is slid over and around the proximal extremity (9) of the pen injection system (10), as the projecting annular flange (21) has a distal surface (22) which comes into abutting engagement with at least part of a proximal surface (23) of the dose setting wheel (11). As can be seen from both FIG. 1 and FIG. 2, the main body (2) is provided with a series of radially spaced apart, raised, sloping shoulders (24) of main body material, which project inwardly into the bore (8) from the inner surface (6), and extend in a distal direction along the inner surface (6) in diminishing thickness from a position distal of the projecting annular flange (21) to the distal extremity (3) of the body (2). The alternating projecting shoulders form a corresponding series of alternating troughs (25). These inwardly projecting and sloping shoulders (24) and corresponding troughs (25) enable the main body (2) to engage in elastic, or frictional, engagement, with the dose setting wheel (11) of the pen injection system, in particular because the dose setting wheels in such pen injection systems often comprise corresponding, outwardly projecting shoulders and corresponding alternating troughs on an outer surface thereof. The two sets of projecting shoulders and troughs can thus engage frictionally with each other, ensuring that rotation of the dose setting wheel (11), or alternatively, the main body (2) causes the other to rotate to the same degree and in the same rotational direction. In an alternative mounting arrangement, the inner surface (6) of the bore would have a layer of elastomer lining said surface in appropriately positioned locations adjacent the distal extremity (3) of the main body (2), and in which said elastomer layer would be brought into frictional or elastic engagement with an outer surface of the dose setting wheel through rotation of a screw-threaded tightening ring or sliding-fit tightening ring mounted on, and located around, the outer surface (7) of the distal extremity (3) of the main body (2).

Figure 3:
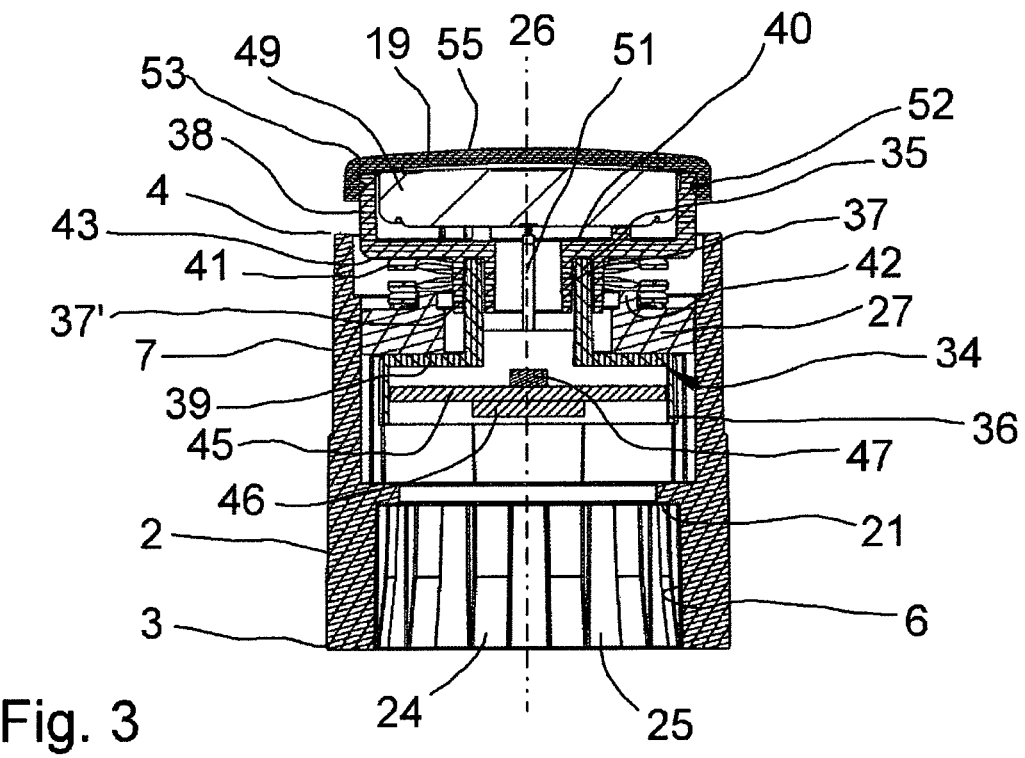
FIG. 3 is a schematic, cross-sectional representation of the injection monitoring module of FIG. 1, in the first monitoring position.
Figure 4:
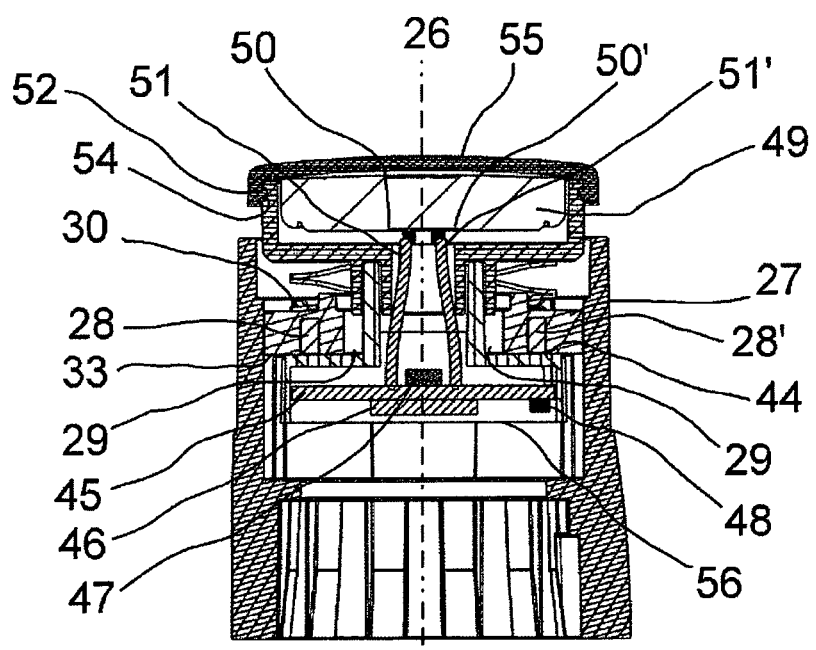
FIG. 4 is a schematic, cross-sectional representation of the injection monitoring module of FIG. 1, rotated by 90°, in the first monitoring position.

FIGS. 3 and 4 are schematic cross-sectional representations of the injection monitoring module as seen along the lines A-A' and B-B' respectively, and showing the injection monitoring module in greater detail, where FIG. 4 along the line B-B' is a 90° rotation about a central longitudinal axis 26 of the main body (2). FIGS. 3 and 4 show the injection monitoring module with the various components in a first position, as they would be just after mounting on a pen injection system, or for example, during dose setting. This relative positioning of the various components of the injection monitoring module also corresponds to the first monitoring position, and also the "engaged" position as described herein. The first monitoring position relates to the first monitoring position of the injection monitoring system, to be described in detail hereunder, and the "engaged" position relates to clutch assembly, also to described in more detail hereunder.

Turning now to FIGS. 3 and 4, a magnetic field producing means (27) is located within the bore (8) about a circumference of the bore (8) and in contact with the inner surface (6) of the body. The magnetic field producing means (27) can be a moulded plastomagnet for example, formed substantially as an annular-shaped disk, or alternatively and preferably, a plastic moulded annular disk into which a pair of single dipole permanent magnets (28, FIG. 4) has been introduced, or encased during moulding of the annular-shaped disk. The magnets (28, FIG. 4) are preferably arranged within the annular-shaped disk in a diametrally opposed N-S/N-S polar arrangement, so that the poles are in alignment across the annular-shaped disk. The disk therefore also comprises a central hole (29) of a diameter which is smaller than that of bore (8). The annular-shaped disk of the magnetic field production means (27) is seated within the main body (2) in a position that is proximal to the annular flange (12) of the body (2), and can be held in place by various different means, for example by one or more inner proximal (30) projections formed on the inner surface (6) of the main body (2), projecting radially from said inner surface (6) at least partly into, and along the length of, the bore (8), to form a proximal sloping shoulder (30a) and distal flange (30b) extending either side of the projecting shoulder (30a). The annular disk (27) is provided with corresponding recesses (31a, 31b, 31c, 31d) located on a peripheral edge (32) of the disk (27), which enter into elastic, or frictional engagement when the disk (27) is inserted, co-axially with the central longitudinal axis (26), into the bore (8) during production assembly of the injection monitoring module (1). The recesses (31a, 31b, 31c, 31d) cooperate with the inner sloping shoulder, and at least part of a distal surface (33) of the disk (27) comes into stopping abutment with the flange (30b) of the proximal sloping shoulder (30a). Due to the frictional contact between the recesses (31a, 31b, 31c, 31d) and the sloping shoulder (30a), on the one hand, and the distal surface (33) and flanges (30b) on the other hand, the annular-shaped disk (27) can not move in any direction along the longitudinal axis, and is, to all intents and purposes, seated immovably within the bore (8) of the body (2).

FIGS. 3 and 4 also show a clutch assembly (17) located within the bore (8) of the main body (2), which extends along the longitudinal axis (26), and at least partly beyond the proximal extremity (4) of the main body, outside of bore (8). The clutch assembly comprises a first, distal body (34), and a second, proximal body (18). The first, distal body (34) and the second, proximal body (18), are connected to each other in a fixed spatial relationship along the central longitudinal axis (26), and are dimensioned so that the first and second bodies can slide, or translate longitudinally along the central longitudinal axis within the bore (8). Both the first, distal (34), and second, proximal (18), bodies have are shaped in the general manner of a goblet with a respective projecting stem (35, 37) and cup (36, 38), with the first, distal body being inverted in comparison to the second, proximal body (18). The stems (35, 37) are substantially hollow and each formed as at least one annular wall projecting away from the respective corresponding bases (39, 40) of the cups (36, 38). In the case of the second, proximal body (18), the stem is formed by a pair of concentric annular walls (37, 37') forming an annular channel into which the stem (35) of the first, distal body is inserted. The stems (35, 37) are held together in fixed relationship for example by adhesive bonding, or ultrasound welding. As can be seen from FIGS. 3 and 4, the stems thereby form an elongated hollow connection member between the first, distal body (34) and the second, proximal body (18), with the distal end of the elongated connection member opening out into the base (39) of cup (36), and the proximal end of the elongated connection member opening out into the base (40) of cup (38). The elongated connection member formed by the stems (35, 37) traverses the central hole (29) of the magnetic field producing means (27), with the result that the first, distal body (34) is located distally of the magnetic field producing means (27), and the second, proximal body (18) is located proximally of said magnetic field producing means (27). The elongated connection member formed by the stems (35, 37) is dimensioned to allow, sliding, or translational movement of the first, distal body (34) and the second, proximal body (18) along the central longitudinal axis (26), such possible longitudinal translation being of a maximum fixed length, for example, of about 15 millimetres in total.

A biasing member (41), for example, a flat wire spring, is positioned distally of the base (40) of the cup (38) of the second, proximal body (18), but proximally of the magnetic field production means (27). The latter is provided with seating projections (42) for seating the biasing member (41), for example, extending from a proximal surface of the disk (27) in a proximal direction along the bore (8). The biasing member (41) is chosen to be able to adopt a relatively constrained or compressed configuration, and a relatively unconstrained, relaxed, or expanded configuration. By default, and equally when the injection monitoring module is first mounted on the pen injection system, the biasing member is in a relatively unconstrained, or relaxed configuration. As the biasing member (41) is seated on the seating projections (42) of the proximal surface of the magnetic field disk (27), and the disk is immovably blocked within the bore (8) of the main hollow body (2), the natural tendency of the biasing member is to exert a pushing force against a distal surface (43) of the base (40) of the cup (38) of the second, proximal body and to engage therewith. This is to be understood as the "engaged" position with regard to the present specification. It also corresponds to the first monitoring position of the injection monitoring module. The counterpart of the biasing member (41) adopting the relatively unconstrained, expanded, or relaxed configuration is that the biasing effect of the biasing member (41) also causes the base (39) of cup (36) of the first, distal body (34) to be moved in a proximal direction along the longitudinal central axis (26), due to the elongated connection member of fixed length formed by the stems (35, 37). As a result, a proximal surface (44) of the base (39) of the first, distal body is brought into abutting contact with the distal surface (33) of the disk of the magnetic field producing means (27).

FIGS. 3 and 4 also show an injection monitoring system. This system is substantially housed within the various components of the clutch assembly. The first, distal body (34) serves as an electronic component board holder body in which an electronic component board (45), such as a printed circuit board, is located, essentially within the cup (36). The electronic component board has a number of electrically connected components, including a micro-controller (46), located on a distal face of the electronic component board, and a magnetometer (47) located substantially in the centre of the proximal face of the electronic component board (45), so that it is aligned with the central longitudinal axis (26). In the respective component positions illustrated in FIGS. 3 and 4, the magnetometer (47) senses and measures the magnetic field produced by the permanent magnets (28)

located in the disk (27) and sends corresponding electrical signals to the micro-controller (46), which is responsible for calculating a series of reference points, and deriving the relative and absolute positions of the magnetometer with regard to the magnetic field producing means (27), which is in a fixed position within the main hollow body (2). The electronic component board (45) also comprises a communications unit (48), such as, for example, a Bluetooth Low Energy circuit, enabling data to be sent and received by the electronic component board to, and respectively from, a remote terminal device, such as a suitably equipped smartphone, remote computing system, or distributed computing system. The second, proximal body (18) serves as a power supply holder body for the injection monitoring system, and to this end receives and locates within the cup (38) thereof an autonomous power supply (49), for example, and as illustrated in the figures, a replaceable lithium ion battery or a removable rechargeable battery. The power supply (49) is connected via electrical connectors (50, 50') located in the cup (38), for example, a suitably located connection plate for the positive and negative terminals of the battery, to a further set of flexible electrical connectors (51, 51'), for example, plastic coated copper wiring, or ribbon connectors, which extend from the connection plate (50, 50') through the elongated connection member formed by the stems (35, 37) to the electronic component board (45). The flexible electrical connectors (51, 51') are designed so as to allow for any possible rotational movement of the clutch assembly around the central longitudinal axis (26) without being damaged and breaking the electrical connection between the electronic component board (45) and the power supply (49). A removable covering cap (19), for example, a push fit cap, engages with an open end of the cup (38) of the second, proximal body (18). In FIGS. 3 and 4, this is shown as a radially inwardly projecting annular ridge (52) provided around an inner peripheral wall (53) of the cap (19), which engages elastically and/or frictionally with a corresponding outer peripheral groove provided on an outer surface of the cup (38) of the second, proximal body to seal the cup (38) opening and prevent ingress of foreign bodies into the cup that might affect the electrical power supply to the component board. Furthermore, the cap (19) provides an outer proximal surface (55) that allows the user to activate the monitoring system and clutch assembly by pushing or pressing down on the outer proximal surface with a digit such as a thumb or finger. The first, distal body (34), is also provided with a distal contact surface (56) that provides a closure for the cup (36) and thereby encase the electronic component board (45) within said first, distal body (34). This distal surface (56) comes into abutting contact with a proximal surface of the injection activator button during operation of the injection monitoring module.

Figure 5:
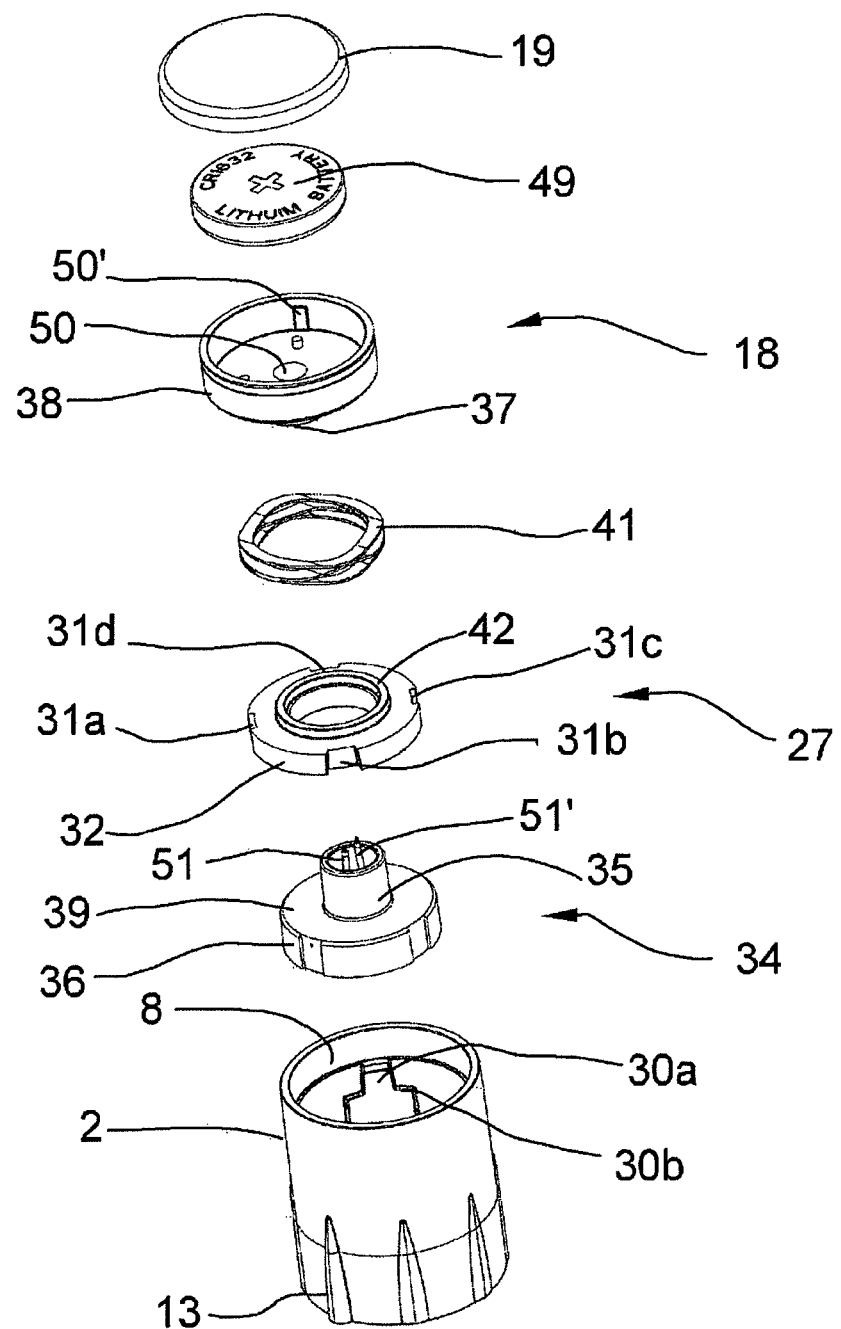
FIG. 5 is a schematic, exploded view of the injection monitoring module according to the invention, along a line of sight from a proximal extremity of said module towards a distal extremity of said module.
Figure 6:
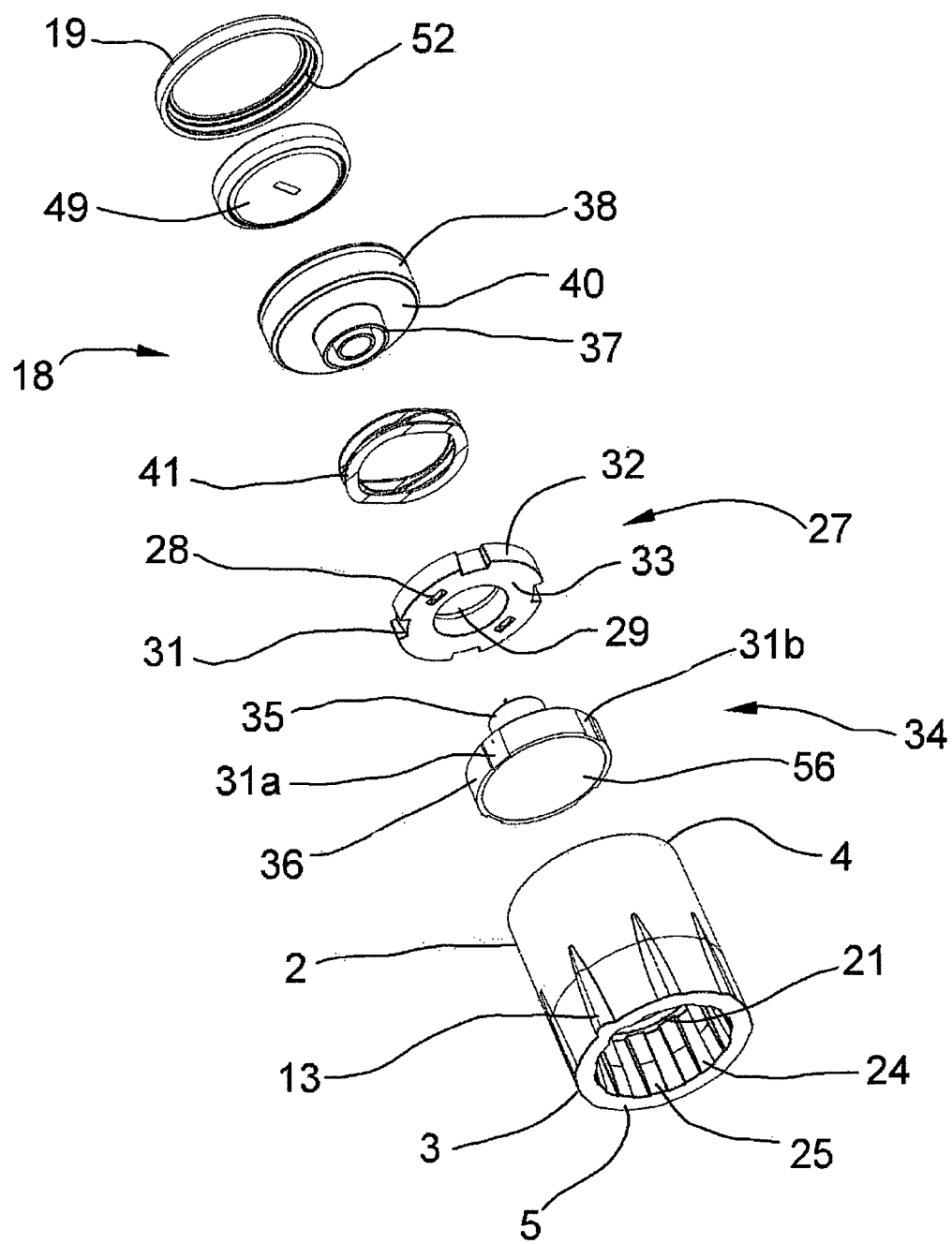
FIG. 6 is a schematic, exploded view of the injection monitoring module according to the present invention, along a line of sight from a distal extremity of said module towards a distal extremity of said module.

FIGS. 5 and 6 show schematic respectively alternative views of the manner in which the various components of the injection monitoring system are arranged along or around the central longitudinal axis (26). Like numbers reference already described features and components of the injection monitoring module as described with regard to the previous figures.

Figures 7A, 7B:
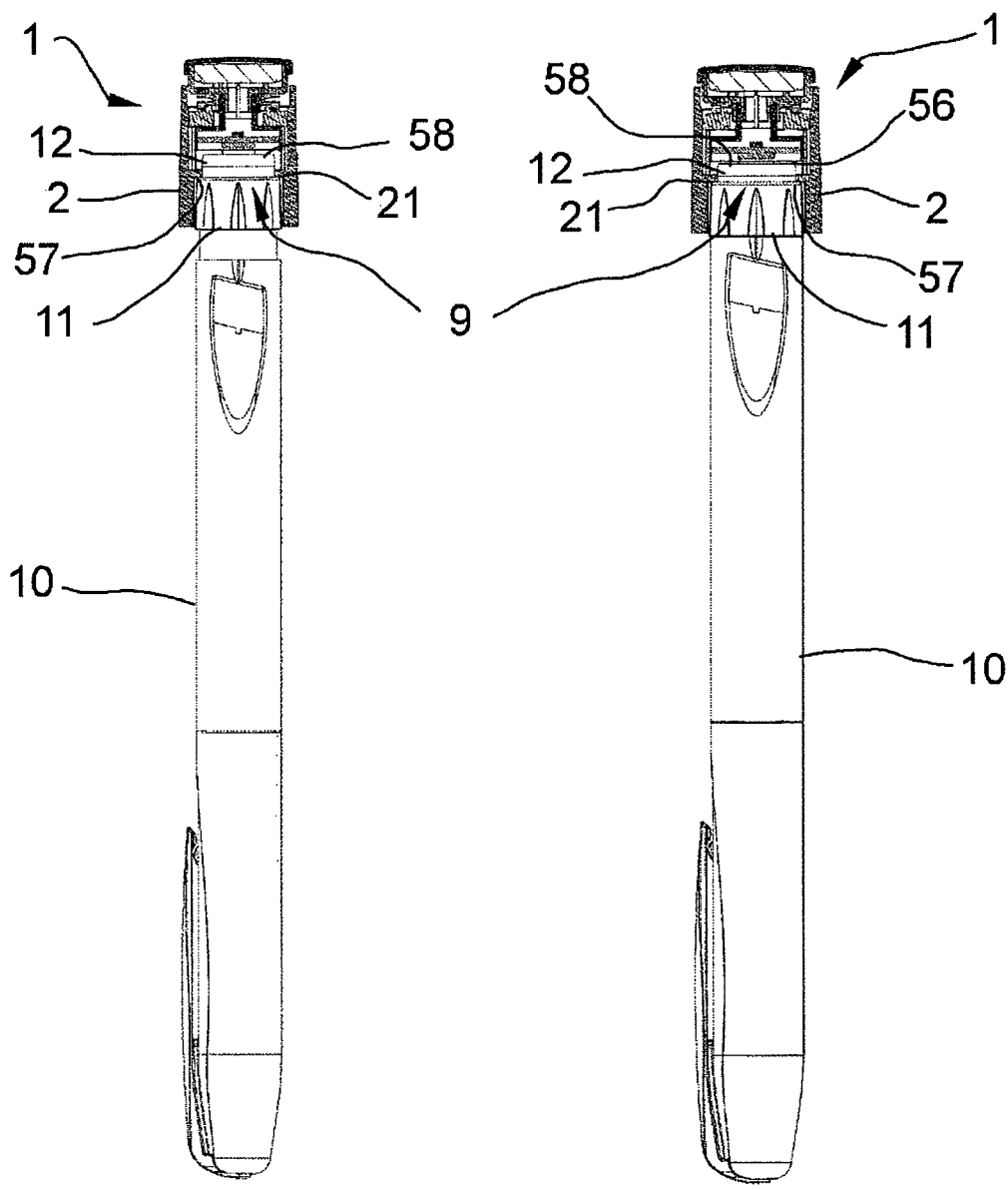
FIGS. 7A and 7B are schematic, cross-sectional representations of the injection monitoring module of the invention, showing the module in the first monitoring position (7A) and the second monitoring position (7B) respectively.

FIGS. 7A and 7B show the relative positioning of the various components of the injection monitoring module during operation thereof, as will be described below.

FIG. 7A is an illustration of the injection monitoring module when mounted on the proximal extremity (9) of a pen injection system (10). The main hollow body (2) surrounds and engages with the dose setting wheel (11) at the distal end (3) of the main body. The body is slid along the central longitudinal axis onto the proximal extremity (9) of the pen injection system (10) until a distal surface of the annular flange (21) of the main body (2) comes into abutting surface contact with a proximal surface (57) of the dose setting wheel (11). One can see in this position that the injection activator button (12) extends in a proximal direction through the reduced diameter created by the annular flange (21) of the main body (2), but a proximal surface (58) of the injection activator is not in abutting contact with the distal surface (56) of the first, distal body (34). Indeed, the biasing element (41) actively pushes the first, distal body (34) away from said proximal surface (58) due to the fixed length connection between the first, distal body (34) and the second, proximal body (18) of the clutch assembly (17). The main body (2) is free to rotate around the central longitudinal axis (26) in co-rotation with the dose setting wheel (11), allowing a user to set the dose to be administered. In this position, the injection monitoring module is considered to be in the first monitoring position, and is registered by the micro-controller, and stored in a volatile or non-volatile memory storage provided either within the micro-controller, or on the electronic component board, for subsequent communication via the communications unit to a remote computing device, such as a suitably equipped smartphone, remote computer or distributed computing system.

The user can activate injection by pressing in a distal direction on the proximal surface (55) of the cap cover (19). As the cap cover (19) is coupled to the cup (38) of second, proximal body (18), any translational force is imparted to the cup (38), and via the contacting abutment of the distal surface of the cup base (40) to the biasing member (41). The second, proximal body (18) thus moves in a distal direction, or translates along, the central longitudinal axis (26), until the limit of compression of the biasing member has been reached. This limit of compression is configured to allow the cup base (39) of the first, distal body (34) due to the fixed length connection between the first, distal body and the second, proximal body, to move away from abutting surface contact with a distal surface (33) of the magnetic field producing means and into abutting contact between the distal contact surface (56) of the cup (39) of the first, distal body (34) with the proximal surface (58) of the injection activator button (12) and to pursue said axial translation along the central longitudinal axis to permit normal functioning of the injection activator button (12) to effect injection of the drug from the pen injection system (10).

As a result of the displacement along the central longitudinal axis, the electronic component board carrying the magnetometer (47) is moved away, in a distal direction, from a position close to the magnetic field producing means, to a position spaced apart therefrom. The displacement, or longitudinal translation of the magnetometer along the central longitudinal axis affects the magnetic field values that the magnetometer captures and signals that are transmitted to the micro-controller. However, due to the central positioning of the magnetometer on the electronic component board which is centrally aligned with the central longitudinal axis, the measured values do not require offset correction calculations by the micro-controller. Furthermore, the relatively small distances travelled by the magnetometer, of the order of approximately 15 millimetres in total, are so small so as not to be affected by any potentially interfering magnetic fields that might otherwise have been caused by any other moving metallic parts that are provided in the most common pen injection systems. As a result, the micro-controller, which is programmed with suitable logic and instructions to perform various calculations, can calculate various reference points from the associated measured and reported magnetic fields, and from those derive absolute and relative positions, without the need for complex correction calculations, and thereby indicate, via an appropriate signal, for example, a LED that lights up, and suitably placed on the electronic component board, or an audible signal produced by appropriate circuitry also provided on the electronic component board, that a desired injection endpoint has been successfully achieved, for example when the selected dose has been fully injected. The micro-controller is also able to calculate any ejected or injected amount of drug, and inform the user thereof by an appropriate signal, such as the LED or audible signal system mentioned above, even in the event that the user releases applied pressure on the cap cover (19), causing the biasing element to move the second, proximal body (18) in a proximal direction back towards the engaged position of the clutch assembly. The communications unit can also be activated at this point in time, or any other suitable point in time, by the micro-controller to send corresponding information or calculation results to a remote device, as indicated above. In this way, the injection monitoring system provides a means for determining, at any given translational point along the central longitudinal axis, whether any drug has actually been injected, and if so, the actual precise amount of injected or ejected drug.

Figure 8:
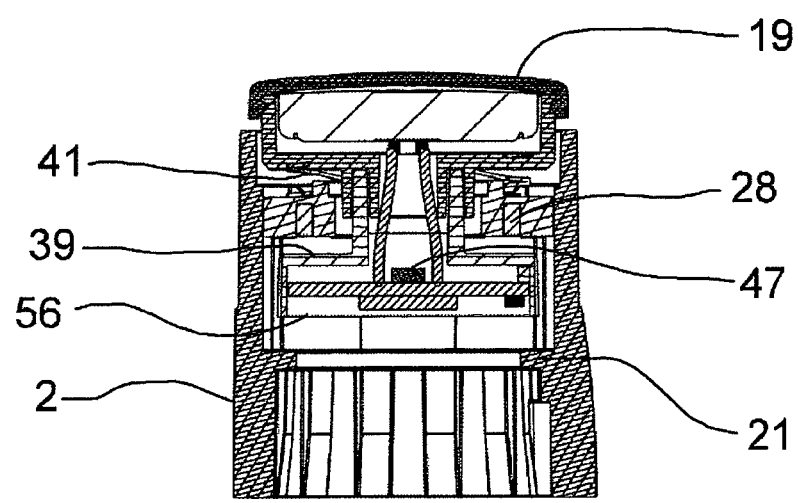
FIG. 8 is a schematic, cross-sectional representation of the injection monitoring module of the invention, showing the module in the second monitoring position.

FIG. 8 is a cross-sectional representation of the injection monitoring module according to the invention once it has reached the second monitoring position. In this figure, it can be seen that the cap cover (19) has been depressed, causing the second, proximal body (18) to move in a distal direction along the central longitudinal axis and compress the biasing member (41) into a constrained configuration, thereby moving the cup base (39) of the first, distal body (34) away from abutting contact with a distal surface (33) of the magnetic field producing means (27), to a clutch assembly disengaged position, in which a distal contact surface (56) of the cup (36) of the first, distal body is now in abutting surface contact with a proximal surface (58) of the injection activator button (12).

When digital pressure on the cap is released once more by the user at the end of the injection, the biasing member (41), as it assumes a relatively unconstrained, or relaxed configuration, biases the cup base (40) of the second, proximal body (18) in a proximal direction along the central longitudinal axis (26), which in turn moves the distal contact surface (56) of the cup (36) of the first, distal body (34) away from abutting surface contact with the proximal surface (58) of the injection activator, until the cup base (39) of the first, distal body comes into abutting contact once again with the distal surface (33) of the disk of the magnetic field production means (17). This return position can also be detected and calculated through the interplay of the magnetometer and the micro-controller, and an appropriate signal given to the user if so desired, for example, to indicate that the system is once again ready for a new dose setting to prepare for a subsequent injection operation.

The invention claimed is:

1. Injection monitoring module adapted and configured to be removably attached to a proximal extremity of a pen injection system for delivery of a drug, the pen injection system being equipped with a proximally located dose setting wheel and injection activator, the dose setting wheel being rotatable about a central longitudinal axis of the pen injection system for dose setting and during injection, wherein the injection monitoring module comprises:

a hollow main body adapted and configured to be coaxially mounted on, and engage in co-rotation with, the dose setting wheel at the proximal extremity of the pen injection system; the hollow main body comprising a central longitudinal bore with a proximal extremity and a distal extremity;

a magnetic field producing means which is seated immovably within the bore of the hollow main body and around the central longitudinal axis; and an injection monitoring system including a magnetometer, said injection monitoring system is located within the central longitudinal bore of the main body at the proximal extremity thereof and extending beyond said proximal extremity along said longitudinal axis in a proximal direction;

wherein the injection monitoring system is movable within the central longitudinal bore of the main body along the central longitudinal axis from a first monitoring position in which the injection monitoring system is not in abutting contact with a proximal surface of the injection activator, to a second monitoring position in which the injection monitoring system is in abutting contact with a proximal surface of the injection activator and wherein said magnetometer is configured to detect changes in magnetic field when said injection monitoring system moves translationally, relative to the magnetic field producing means, between said first and second monitoring positions.

2. Injection monitoring module according to claim 1, wherein said magnetic field producing means comprises two diametrically aligned single dipole magnets.

3. Injection monitoring module according to claim 1, wherein said magnetometer comprises a single magnetic field sensor.

4. Injection monitoring module according claim 1, wherein said magnetometer is a single magnetic field sensor which is located on the central longitudinal axis, and is movable along said axis from a first proximal position to a second distal position along said axis.

5. Injection monitoring module according to claim 1, wherein the injection monitoring system comprises an electronic component board, and wherein said magnetometer is electrically connected to the electronic component board, and wherein the electronic component board comprises at least one micro-controller in electrical connection with the magnetometer.

6. Injection monitoring module according to claim 1, wherein said magnetometer is located on a proximal face of an electronic component board.

7. Injection monitoring module according to claim 1, wherein an electronic component board comprises a communications unit in electrical connection with at least one microcontroller.

8. Injection monitoring module according to claim 1, wherein a clutch assembly comprises a first, distal body and a second, proximal body, and further comprises a biasing member located between the first, distal body and the second, proximal body.

9. Injection monitoring module according to claim 1, wherein comprising a clutch assembly which comprises a first, distal body and a second, proximal body, and first, distal body is an electronic component board holder body.

10. Injection monitoring module according to claim 1, comprising a clutch assembly which comprises a first, distal body and a second, proximal body, and wherein the second proximal body is a power supply holder body.

11. Injection monitoring module according to claim 1, comprising a clutch assembly which comprises a first, distal body and a second, proximal body, and wherein the first, distal body, and the second, proximal body are connected together along the central longitudinal axis via an elongated hollow connecting member.

12. Injection monitoring module according to claim 1, comprising a clutch assembly which comprises a first, distal body and a second, proximal body, and wherein the first, distal body, and the second, proximal body are connected together along the central longitudinal axis via an elongated hollow connecting member, wherein an electronic component board and a power supply are electrically connected via said elongated hollow connecting member.

13. Injection monitoring module according to claim 1, comprising a clutch assembly which comprises a first, distal body and a second, proximal body, and wherein the first, distal body is located distally of said magnetic field producing means.

14. Injection monitoring module according to claim 1, comprising a clutch assembly which comprises a first, distal body and a second, proximal body, and wherein the second, proximal body is located proximally of the magnetic field producing means.

15. Injection monitoring module according to claim 1, comprising a clutch assembly which comprises a first, distal body and a second, proximal body, and wherein a biasing member is located proximally of said magnetic field producing means and distally of the second, proximal body.

16. Injection monitoring module according to claim 1, wherein said magnetic field producing means comprises a distal surface that is in contact with a proximal surface of an electronic component board body when a clutch assembly is in a first, engaged position, and wherein said proximal surface of the electronic component board body is axially spaced apart along the central longitudinal axis from said distal surface of the magnetic field producing means when the clutch assembly is in the second, disengaged position.

17. Process for calculating an actual amount of drug ejected or injected from a pen injection system comprising:
mounting the injection monitoring module comprising the injection monitoring system according to claim 1, to the proximal extremity of the pen injection system for delivery of the drug, the pen injection system being equipped with the proximally located dose setting wheel and the injection activator, the dose setting wheel being rotatable about the central longitudinal axis of the pen injection system for dose setting and during injection;
setting a dose via rotation of the dose setting wheel;
activating the injection activator to effect an injection;
determining an injected dose from a translational movement of the injection monitoring system caused by activation of the injection activator, from the first monitoring position in which the injection monitoring system is not in abutting contact with the proximal surface of the injection activator, to the second monitoring position in which the injection monitoring system is in abutting contact with the proximal surface of the injection activator.

* * * * *